(12) United States Patent
Ram et al.

(10) Patent No.: US 9,823,188 B1
(45) Date of Patent: Nov. 21, 2017

(54) SYSTEMS AND METHODS FOR DETECTING THE PRESENCE OF A CONTAMINANT

(71) Applicants: Manoj Kumar Ram, Tampa, FL (US); Muhammad Rahman, Tampa, FL (US)

(72) Inventors: Manoj Kumar Ram, Tampa, FL (US); Muhammad Rahman, Tampa, FL (US)

(73) Assignee: University of South Florida, Tampa, FL (US)

( * ) Notice: Subject to any disclaimer, the term of this patent is extended or adjusted under 35 U.S.C. 154(b) by 78 days.

(21) Appl. No.: 14/834,508

(22) Filed: Aug. 25, 2015

Related U.S. Application Data

(60) Provisional application No. 62/047,907, filed on Sep. 9, 2014.

(51) Int. Cl.
*G01N 21/3577* (2014.01)
*G01N 21/94* (2006.01)
*G01N 21/31* (2006.01)

(52) U.S. Cl.
CPC ..... *G01N 21/3577* (2013.01); *G01N 21/3103* (2013.01); *G01N 21/94* (2013.01); *G01N 2201/061* (2013.01); *G01N 2201/12* (2013.01)

(58) Field of Classification Search
CPC ................................. G01N 21/3577
See application file for complete search history.

(56) References Cited

U.S. PATENT DOCUMENTS

| | | | |
|---|---|---|---|
| 3,811,778 A * | 5/1974 | Hadeishi | G02B 5/3083 356/312 |
| 4,732,475 A | 3/1988 | Harrick | |
| 5,581,085 A | 12/1996 | Reffner et al. | |
| 6,587,575 B1 * | 7/2003 | Windham | G01N 21/31 250/458.1 |
| 2002/0071116 A1 * | 6/2002 | Bjork | G01N 21/94 356/238.1 |
| 2002/0185604 A1 * | 12/2002 | Coates | G01J 3/443 250/339.09 |
| 2003/0232448 A1 * | 12/2003 | Shelley | G01B 11/0616 436/164 |

(Continued)

FOREIGN PATENT DOCUMENTS

| | | |
|---|---|---|
| WO | 2013025679 | 2/2013 |
| WO | 2013148656 | 10/2013 |

OTHER PUBLICATIONS

Sobanska et al., Microchemical Investigations of Dust Emitted by a Lead Smelter, Mar. 1999, Environmental Science & Technology Journal, vol. 3 No. 9, pp. 1334-1339.*

(Continued)

*Primary Examiner* — David Porta
*Assistant Examiner* — Jeremy S Valentiner
(74) *Attorney, Agent, or Firm* — Thomas | Horstemeyer, LLP

(57) ABSTRACT

In some embodiments, a system for detecting the presence of a contaminant on a surface includes an infrared light source configured to shine infrared light on the surface, an infrared light detector configured to detect infrared light reflected from the surface, and a computing device configured to receive an infrared reflectance signal from the infrared light detector and detect the presence of the contaminant from a feature in the reflectance signal.

13 Claims, 8 Drawing Sheets

(56) References Cited

U.S. PATENT DOCUMENTS

| | | | | |
|---|---|---|---|---|
| 2005/0124074 A1* | 6/2005 | Shelley | .............. | G01N 21/3563 |
| | | | | 436/178 |
| 2007/0139648 A1* | 6/2007 | Singh | ................... | G01N 21/553 |
| | | | | 356/337 |
| 2007/0162992 A1* | 7/2007 | Burns | ................... | G01N 21/31 |
| | | | | 800/21 |
| 2010/0239821 A1* | 9/2010 | Nagao | .................... | G01N 21/35 |
| | | | | 428/172 |
| 2013/0140463 A1* | 6/2013 | Myrick | ................. | G01N 21/55 |
| | | | | 250/341.8 |
| 2013/0265568 A1* | 10/2013 | Micheels | ............. | G01N 21/359 |
| | | | | 356/51 |
| 2016/0025620 A1* | 1/2016 | Lansel | ................ | G01N 21/255 |
| | | | | 702/25 |

OTHER PUBLICATIONS

Gremlich, et al., "Use of FT-IR internal reflection spectroscopy in combinatorial Chemistry", Applied spectroscopy 50.4, 1996.
FT-NIR Principle and Application; Shimadzu (Asia Pacific) Pte Ltd, 1996.

* cited by examiner

SYSTEMS AND METHODS FOR DETECTING THE PRESENCE OF A CONTAMINANT

CROSS-REFERENCE TO RELATED APPLICATION

This application claims priority to U.S. Provisional Application Ser. No. 62/047,907, filed Sep. 9, 2014, which is hereby incorporated by reference herein in its entirety.

BACKGROUND

Lead is used in various industrial and consumer applications, including lead-acid batteries, photovoltaic solar installation, telecommunications equipment, computer systems, and electric vehicles. The most common application by far, however, is its use in lead-acid batteries. Approximately 80% of lead mined in the world is used in battery applications. Around 60,000 to 70,000 people are employed worldwide in the battery manufacturing industry and are directly exposed to lead.

When the concentration of lead builds in the body, it can cause serious health-related issues such as headaches, irritability, reduced sensations, aggressive behavior, difficulty in sleeping, anemia, constipation, and poor appetite. Furthermore, children exposed to lead can suffer kidney damage, hearing loss, loss of developmental skills, behavior attention problems, and reduced intelligence quotient (IQ). It is therefore critical to be able to detect the presence of lead contaminants to limit such exposure.

Lead contaminants can be detected using various techniques, including atomic absorption spectrometry (AAS), inductive coupled plasma mass spectrometry (ICP-MS), inductive coupled plasma atomic emission spectrometry (ICP-AES), dynamic light scattering (DLS), enzyme-linked immunosorbent assays (ELISAs), reversed-phase high-performance liquid chromatography coupled with UV-Vis or fluorescence detection, voltammetry, and fluorimetric techniques. Unfortunately, each of these techniques is time consuming, labor intensive, and requires a professional to perform the testing. In addition, many of these techniques require expensive instruments. In view of these drawbacks, the test most commonly applied in lead-acid battery factories is a swipe test in which the exposure of the skin to lead contaminants is determined by wiping the skin with a patch and applying a compound to the patch that reacts with the lead. In some detection kits used at such factories, sodium sulfide is applied to the patch, which turns yellow when lead ions are present in a concentration of approximately 1 to 3 parts per million (ppm) and turns dark when lead ions are present in a concentration greater than 50 ppm. Other detection kits use a solution of sodium rhodizonate ($C_6H_2O_6 \cdot 2H_2O$), which reacts with $Pb^{+2}$ ions and forms a pink to red color because of the formation of lead rhodizonate. While such kits are simple and inexpensive, they lack standardization, do not provide highly accurate results, and can provide false positive results.

In view of the above discussion, it can be appreciated that it would be desirable to have a system and method for detecting contaminants, such as lead contaminants, that is simple, accurate, and inexpensive.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a system and method for detecting contaminants, such as lead contaminants, that is simple, accurate, and inexpensive. Disclosed herein are examples of systems and methods that can be used to detect not only lead contaminants but other potentially harmful metal contaminants, such as other transition metals (e.g., titanium, iron, cobalt, and manganese), heavy metals (e.g., cadmium, mercury, copper, arsenic, and zinc), and heavy metal oxides, sulfates, halides, and carbonates. In one embodiment, a contaminant detection system comprises an infrared (IR) light source, an IR light detector, and a computing device that is in communication with the light detector. A surface, such as a skin surface, can be illuminated with IR light from the light source and the IR light reflected from the surface can be detected by the IR light detector. The reflectance signature of this light can be analyzed by the computing device to determine which contaminants, if any, are present on the surface, and at what concentration. In some embodiments, a reflectance medium is applied to the surface to be tested to increase the IR reflectance of the surface and at what concentration. In some embodiments, the reflectance medium comprises a liquid that contains small metallic particles.

In the following disclosure, various specific embodiments are described. It is to be understood that those embodiments are example implementations of the disclosed inventions and that alternative embodiments are possible. All such embodiments are intended to fall within the scope of this disclosure.

As described above, the most common use of lead is in the manufacture of lead-acid batteries. Lead-acid batteries contain various lead-based materials, such as lead (Pb), lead oxide (PbO), lead tetroxide ($Pb_3O_4$), lead sulfate ($PbSO_4$), and various lead-based chemical species (e.g., $PbO.PbSO_4$, $3PbO.PbSO_4.H_2O$, and $4PbO.PbSO_4$). These lead-based materials and other heavy metal contaminants have distinct IR reflectance properties. Because of this, the presence of such contaminants can be detected by sensing their IR reflectance signatures. As described below, the IR reflectance signatures of various lead contaminants were evaluated by measuring the reflectance spectra from 600-150 $cm^{-1}$, 950 to 2000 $cm^{-1}$, and 4,000-8,000 $cm^{-1}$. Through this evaluation, the infrared spectra of PbO (tetragonal), PbO (orthorhombic), $Pb_3O_4$, $PbSO_4$, $PbO.PbSO_4$, $3PbO.PbSO_4.H_2O$, and $4PbO.PbSO_4$ were each found between 500 to 170 $cm^{-1}$. The reflection IR signal intensity changes with the concentration of each lead-based material.

Figure 1:
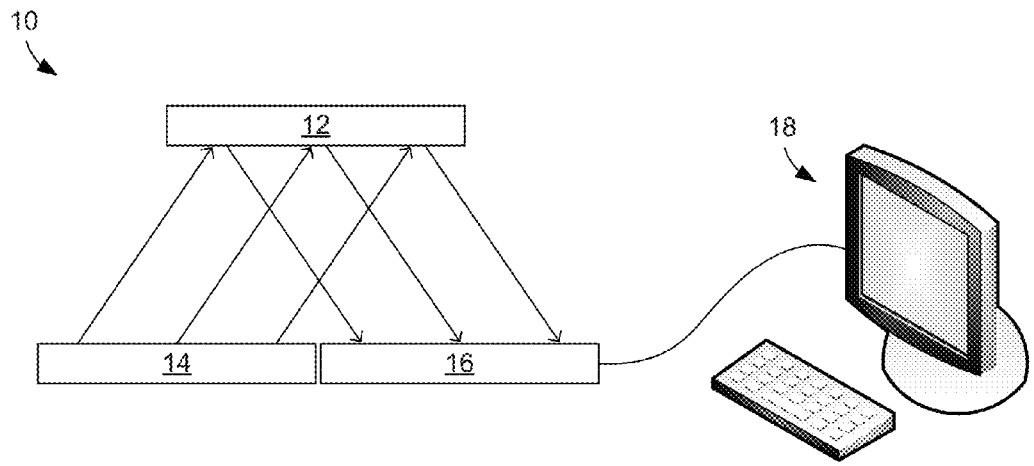
FIG. 1 is a schematic view of an embodiment of a system for detecting the presence of a contaminant.

FIG. 1 illustrates a contaminant detection system 10 with which the presence of a contaminant on an object 12, such as a hand, can be detected. As shown in the figure, the system 10 generally comprises an IR light source 14, an IR light detector 16, and a computing device 18 that is in communication with the IR light detector. In some embodiments, the IR light source emits infrared light in the range of 700 to 200 $cm^{-1}$ (i.e., a wavelength range of approximately 14 to 50 μm). In some embodiments, the IR light source 14 comprises multiple IR light emitting diodes (LEDs) each emitting light at a different wavelength range within the IR spectrum. In some embodiments, the IR light detector 16 comprises a $LiTaO_3$ detector.

Figure 2:
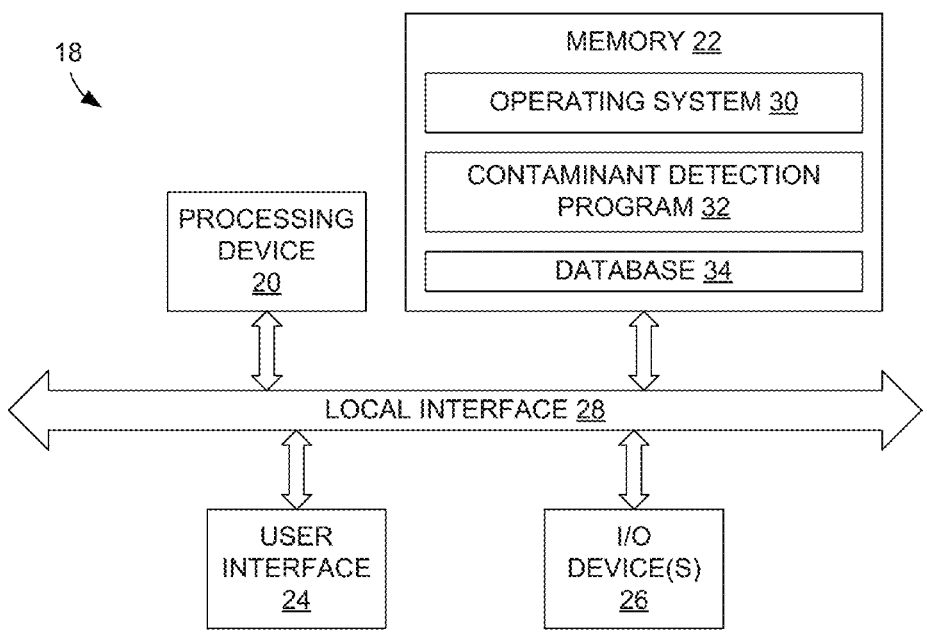
FIG. 2 is a block diagram of an example configuration for a computing device shown in FIG. 1.

Although the computing device 18 is depicted in FIG. 1 as a desktop computer, it is noted that the computing device can comprise any device having adequate computing capabilities, such as a laptop computer, a tablet computer, a handheld computer (e.g., smart phone), or the like. FIG. 2 illustrates an example configuration for the computing device 18. As shown in this figure, the computing device 18 includes a processing device 20, memory 22, a user interface 24, and at least one I/O device 26, each of which is connected to a local interface 28.

The processing device 20 can include a central processing unit (CPU) or a semiconductor-based microprocessor (in the form of a microchip). The memory 22 includes any one of or a combination of volatile memory elements (e.g., RAM) and nonvolatile memory elements (e.g., hard disk, ROM, Flash, etc.). The user interface 24 comprises the components with which a user interacts with the computing device 18, such as a keyboard, keypad, and/or display screen, and the I/O devices 26 are adapted to facilitate communications with other devices.

The memory 22 (a non-transitory computer-readable medium) comprises programs (logic) including an operating system 30 and a contaminant detection program 32 that comprises one or more algorithms that are configured to process the signals (spectra) received from the IR light detector to determine whether or not a contaminant is present and in what quantity. In addition, the memory 22 comprises a database 34 that can include the IR signatures of various contaminants for purposes of comparison.

When a surface, such as the surface of an individual's skin, is to be tested for the presence of a contaminant, such as a heavy metal contaminant like lead, the surface is illuminated with light emitted from the IR light source 14 and the IR light that is reflected from the surface is captured by the IR light detector 16. As described below, a reflectance medium can be applied to the surface to enhance the reflection of the IR light onto the detector 16. The signals captured by the IR light detector are transmitted to the computing device 18, which executes the contaminant detection program 32 to identify features in the signals, such as spikes, that are indicative of the presence of one or more particular contaminants. In some embodiments, the concentrations of the contaminants are also calculated by the program 32. The entire test, including illumination of the surface and processing of the reflected signals, can be performed in a few seconds to a few minutes. This is far superior to the swipe method currently used in lead-acid battery factories and the test can be performed much more quickly and inexpensively than other lead detection methods typically used in the laboratory.

PbO, $PbSO_4$, and PbS (i.e., lead contaminants) were selected as target contaminants for testing purposes using Fourier transform infrared (FTIR) spectroscopy. Such lead compounds were initially tested using a polyethylene (PE) membrane to understand the IR pattern of the lead contaminants. Attempts were taken to understand the lead contaminants using the chicken skin to simulate the lead contamination on human skin.

Figure 3:
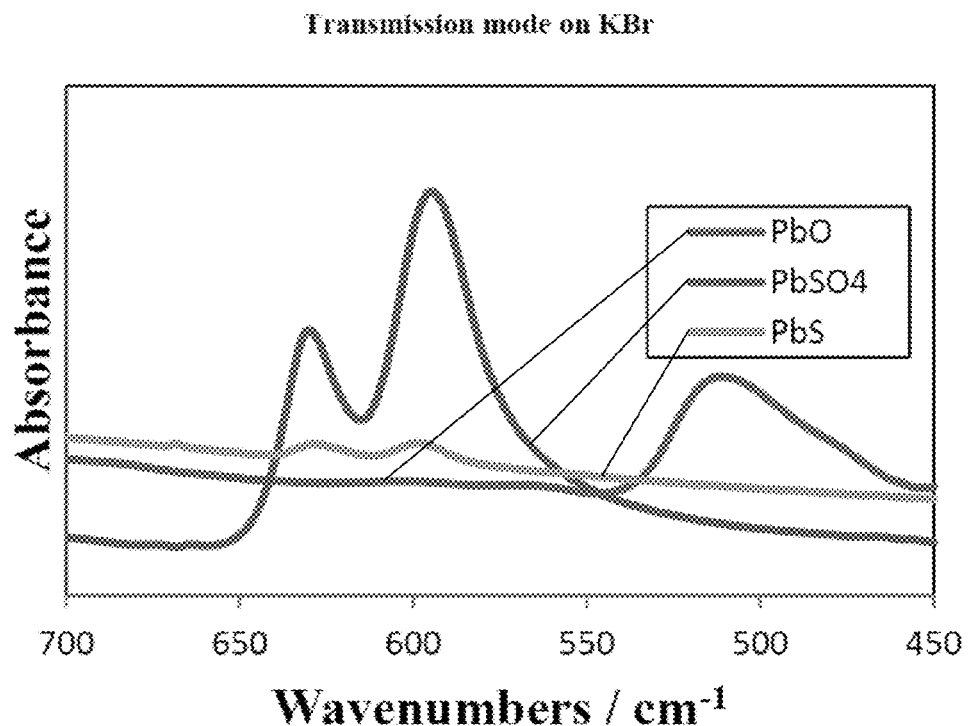
FIG. 3 is a graph that shows Fourier transform infrared (FTIR) spectra of lead contaminants on potassium bromide (KBr) from 450 $cm^{-1}$ to 700 $cm^{-1}$ in transmission mode.
Figure 4:
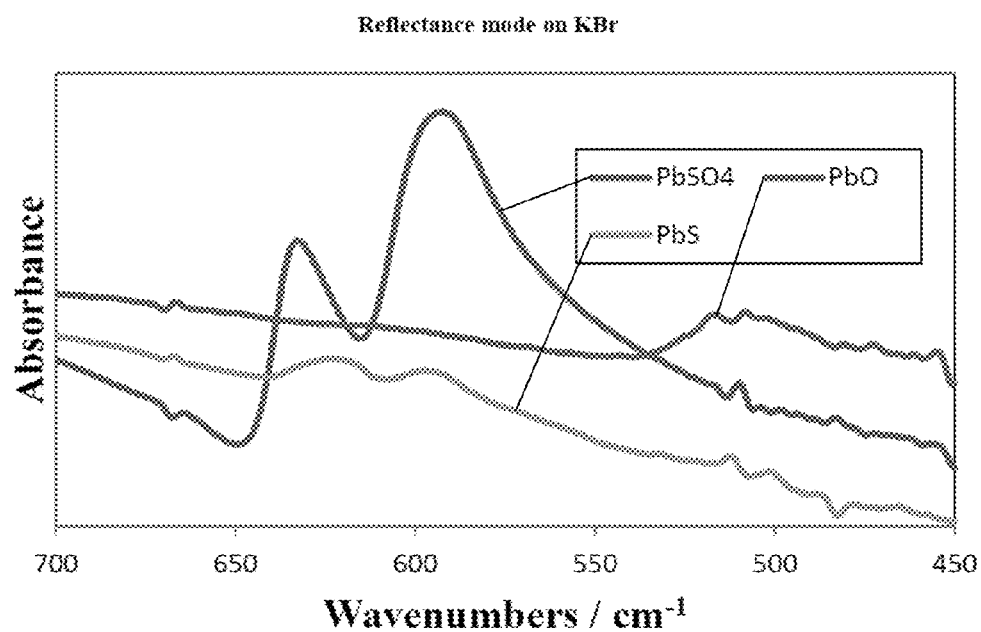
FIG. 4 is a graph that shows FTIR spectra of lead contaminants on KBr from 450 $cm^{-1}$ to 700 $cm^{-1}$ in reflectance mode.

Potassium bromide (KBr) is a suitable substrate for experiments due to its excellent transmission properties from 700 $cm^{-1}$ to 450 $cm^{-1}$. Three kinds of target materials (PbO, $PbSO_4$, and PbS) were characterized using a KBr substrate to determine the characteristic lead contaminant peaks. FIGS. 3 and 4 show the characterization peaks of the three lead contaminants in the selected region under transmission and reflectance mode.

Polyethylene is an IR-transparent polymeric material. The lead contaminants' infrared characteristics were initially measured using a polyethylene membrane. There are three bands in the prism region of 3200 to 700 $cm^{-1}$ for polyethylene membranes. The infrared signal absorption bands at 2950 $v_a(CH_2)$, $\delta(CH_2)$ 1470, and $\gamma_w(CH_2)$ 731 $cm^{-1}$. Therefore, the membrane is useful to understand the peak between 700-400 $cm^{-1}$. PbO, PbSO4, and PbS were separately applied to the polyethylene membrane at different concentrations and the infrared spectra were recorded in both transmission and reflection modes. The characterization peaks are summarized in Table 1.

TABLE 1

Characterization peaks of three lead contaminants.

| PbO | $PbSO_4$ | PbS |
|---|---|---|
| 511 | 595/630 | 598/629 |
| 508 | 593/630 | 598/624 |
| 506 | 596/633 | 598/532 |

Figure 5:
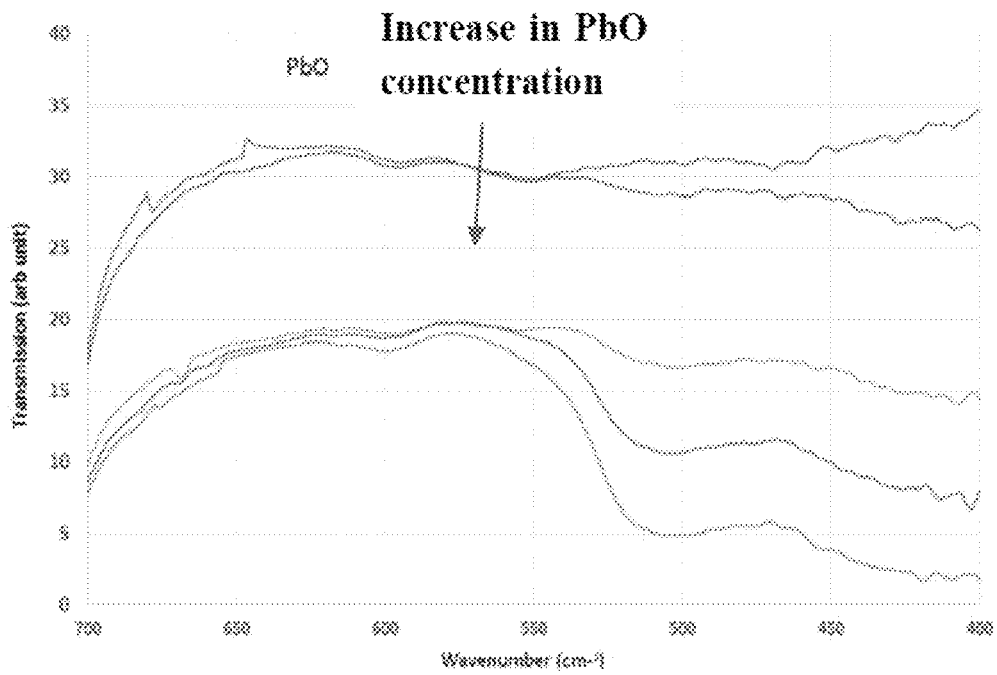
FIG. 5 is a graph that shows FTIR spectra of lead oxide (PbO) using a polyethylene (PE) membrane.
Figure 6:
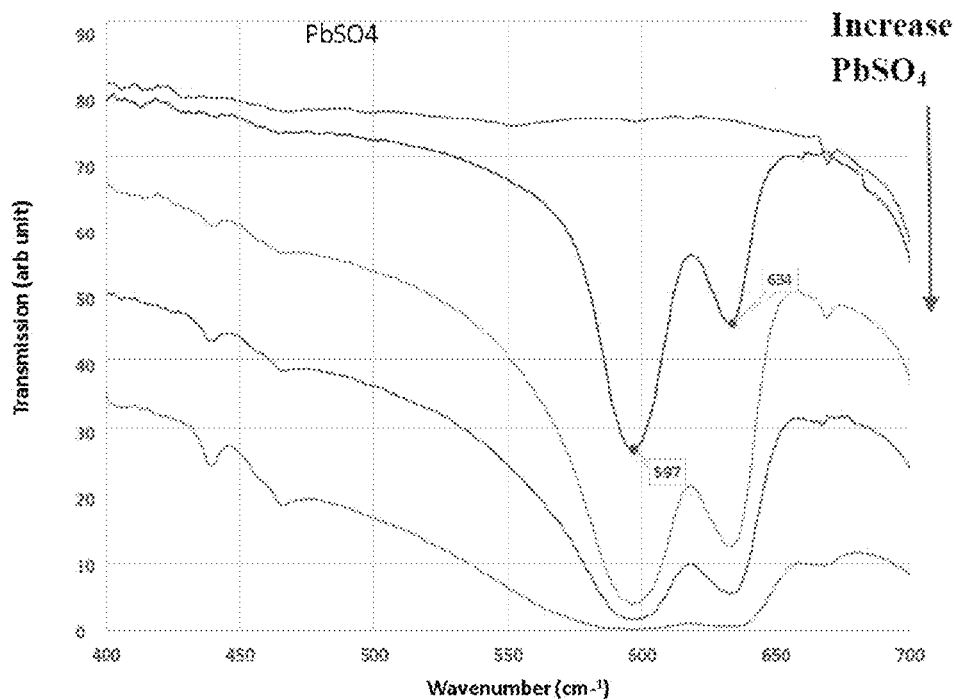
FIG. 6 is a graph that shows FTIR spectra of lead sulphate ($PbSO_4$) using a PE membrane.
Figure 7:
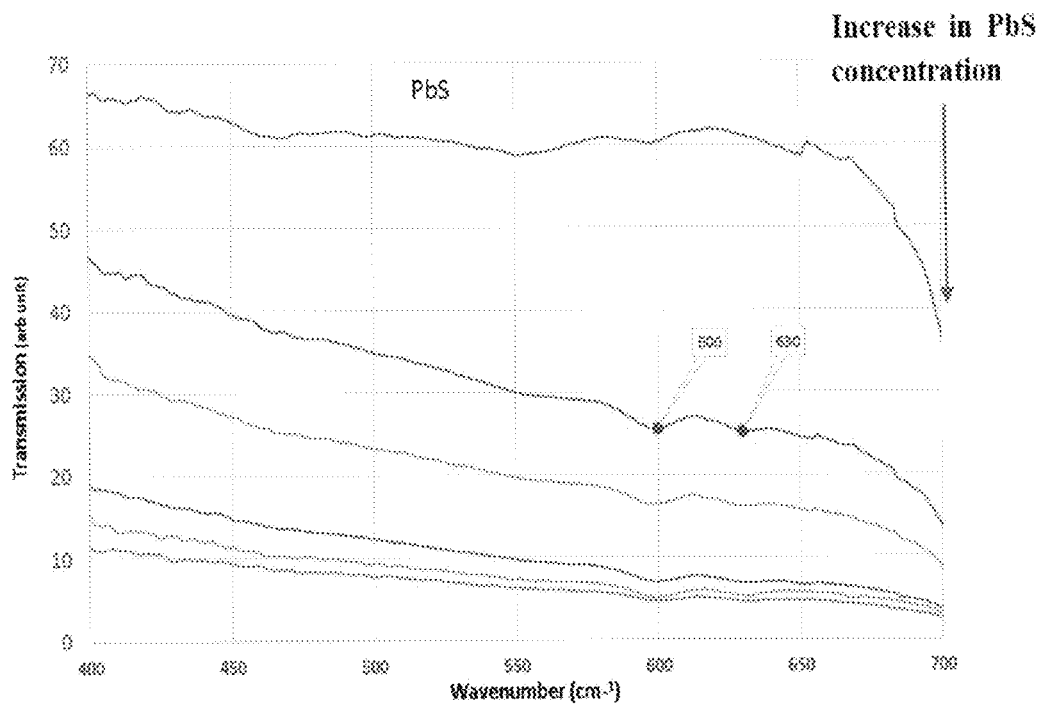
FIG. 7 is a graph that shows FTIR spectra of lead sulfide (PbS) using a PE membrane.

The polyethylene membranes were formed by heating and pressing polyethylene between two flat metal plates. The membranes were removed from the metal surfaces using a blade. PbO, $PbSO_4$, and PbS were used on the membrane at different concentrations and the IR spectra were measured in the reflection mode. It was found that the IR absorption changed as a function of the lead concentration with defined peaks due to the presence of the PbO, $PbSO_4$, and PbS (see FIGS. 5-7). Different concentrations of PbO, $PbSO_4$, PbS were used on the polyethylene membrane. The increase in the infrared absorption is apparent in FIGS. 5-7. As shown in these figures, as the concentration of the lead contaminant increased, the transmitted signal decreased.

Figure 8:
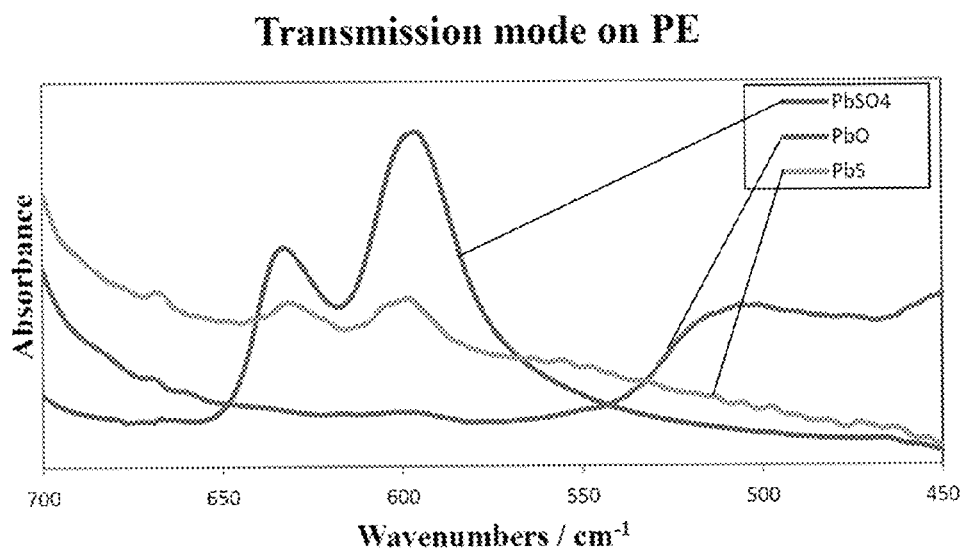
FIG. 8 is a graph that shows FTIR spectra of lead contaminants on PE from 450 $cm^{-1}$ to 700 $cm^{-1}$ in transmission mode.

FIG. 8 shows the FTIR spectra of the lead contaminants on polyethylene from 450 $cm^{-1}$ to 700 $cm^{-1}$ in transmission mode. The y-axis has been plotted in absorption mode. As PbSO$_4$ is white-gray in color, it reflects more than PbO and PbS and better peaks were observed. Because PbS is black, it absorbs the IR signal and provides minimal reflection. In transmission mode, PbO showed peaks at 608, 598, and 509 cm$^{-1}$, PbSO$_4$ showed peaks at 633 and 596 cm$^{-1}$, and PbS showed peaks at 667, 630 and 598 cm$^{-1}$.

Figure 9:
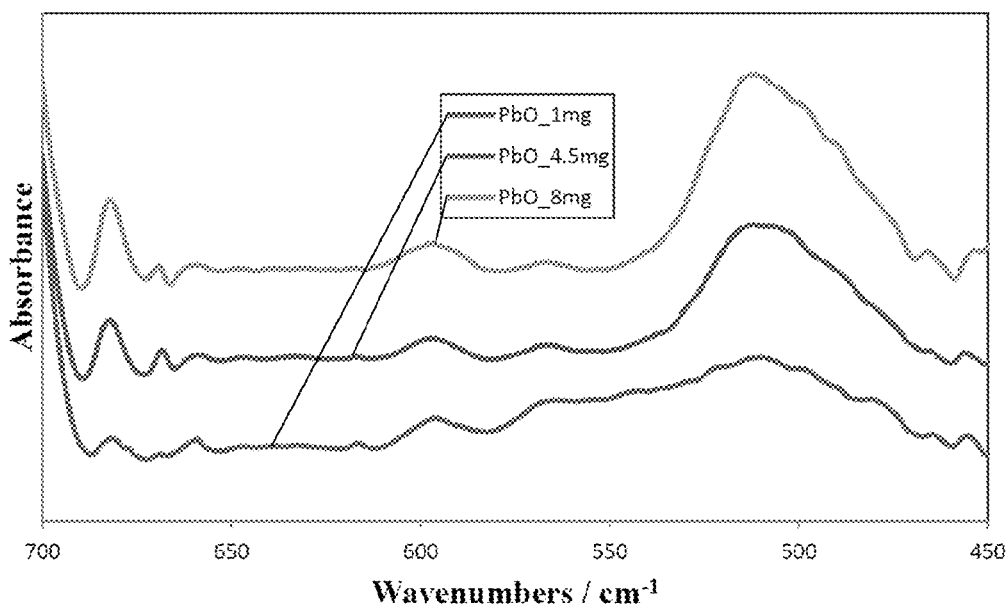
FIG. 9 is a graph that shows FTIR spectra of PbO on PE membrane 450 $cm^{-1}$ to 700 $cm^{-1}$ in reflectance mode.
Figure 10:
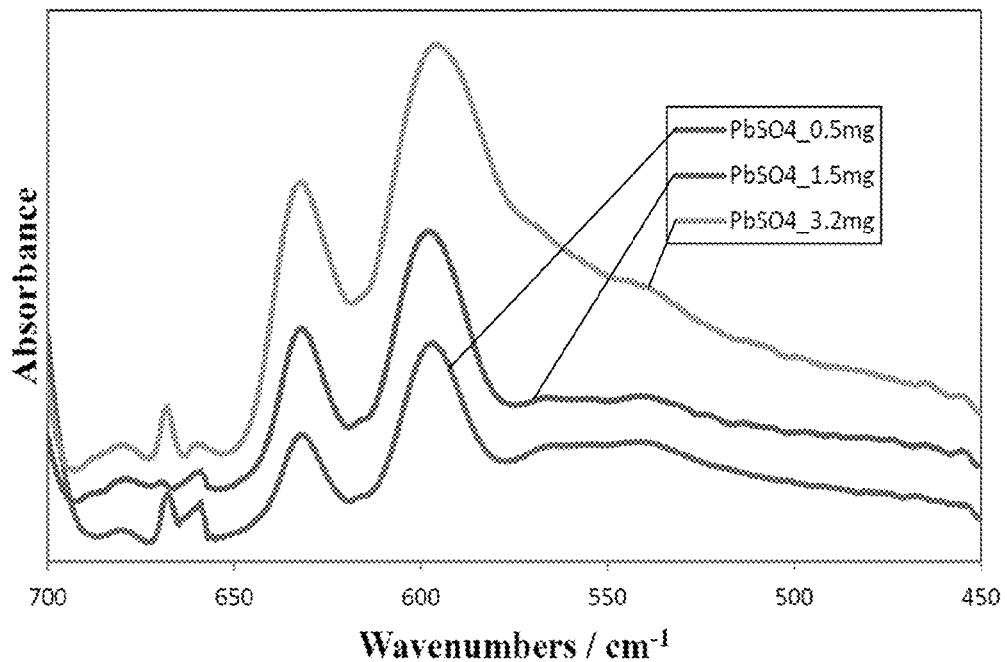
FIG. 10 is a graph that shows FTIR spectra of $PbSO_4$ on PE membrane 450 $cm^{-1}$ to 700 $cm^{-1}$ in transmission mode.
Figure 11:
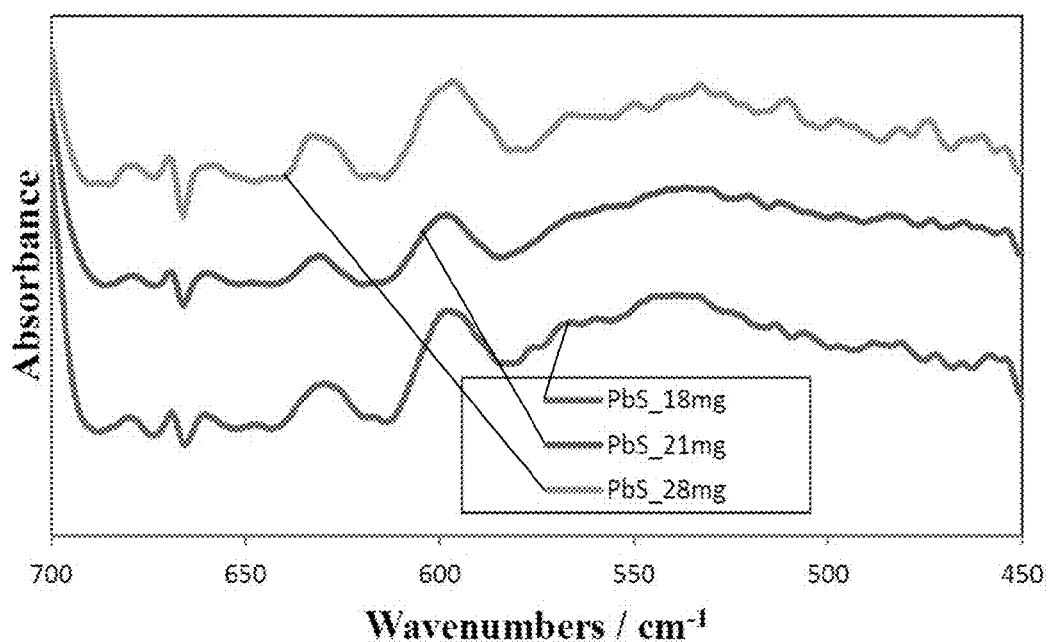
FIG. 11 is a graph that shows FTIR spectra of PbS on PE membrane 450 $cm^{-1}$ to 700 $cm^{-1}$ in reflectance mode.

Next, the lead contaminants were evaluated in reflectance mode. It was determined that PbO (FIG. 9), PbSO$_4$ (FIG. 10), and PbS (FIG. 11) each systematically reflect the infrared signal. The increase in IR absorption can be seen in FIGS. 9-11 for increasing concentrations of PbO, PbSO$_4$, and PbS on the polyethylene membrane. Because of their colors, PbO and PbSO$_4$ are able to reflect more infrared signal, while PbS absorbed the infrared signal with minimal reflection. However, a similar pattern was observable for PbS when a high enough concentration was used, as shown in FIG. 11.

Unlike polyethylene membranes, skin is uneven and contains water. It is typically difficult to perform FTIR spectroscopy on human skin because its reflectivity is low. In particular, human skin can only reflect 0.1% of incident infrared. In such a case, the characteristic peaks will be immersed in the background signal and it is nearly impossible to detect any compound by analyzing characteristic peaks.

Figure 12:
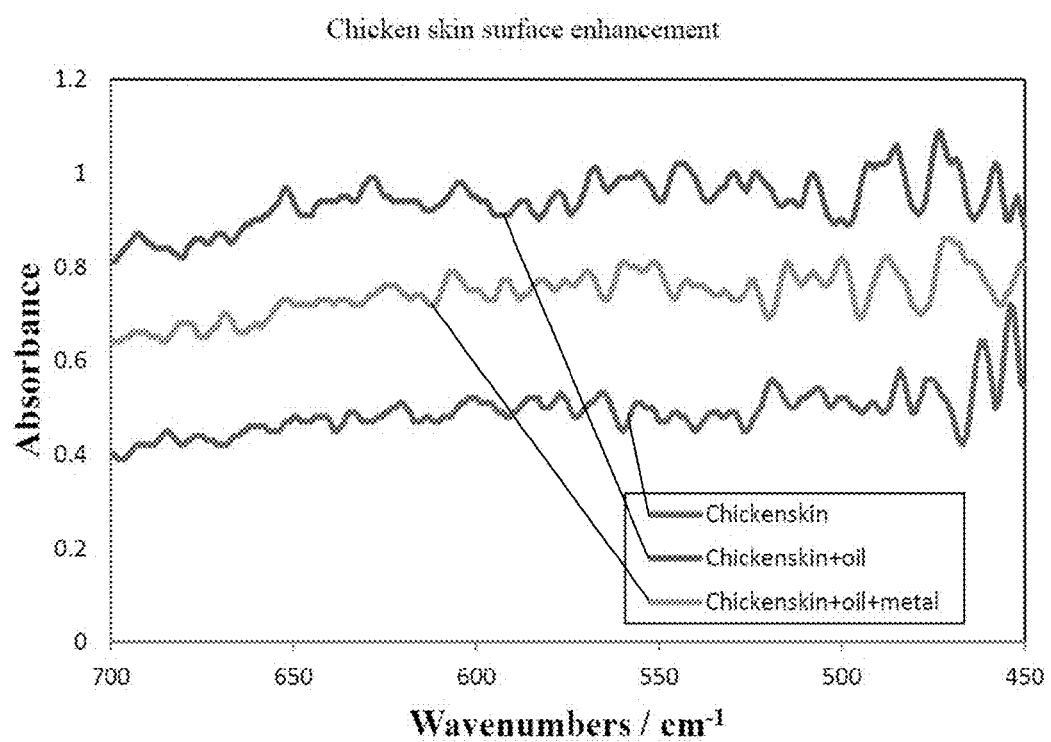
FIG. 12 is a graph that shows the surface reflectivity of chicken skin enhanced with a reflectance medium.

In order to solve this problem, a reflectance medium can be applied to the skin to increase its IR reflectance. During the experimentation, olive oil and vegetable oil were mixed with metallic nanoparticles (i.e., tungsten nanoparticles) to create such a medium. The mixture was then applied to chicken skin, which was used to simulate the human skin. The application of the reflectance medium has two effects. First, it seals the water content under the oil and prevents it from interfering with the IR signal. The water-oil interface also increases the reflectivity to infrared. Second, the metallic nanoparticles, which have high reflectivity, enhance the reflected infrared signal. As shown in FIG. 12, the reflectivity of chicken skin is increased when oil and a mixture of oil and metallic nanoparticles are applied to the skin. In particular, the reflectively is increased from 0.4% with skin alone to 0.6% when oil is added and 1% when oil/nanoparticles are added.

Figure 13:
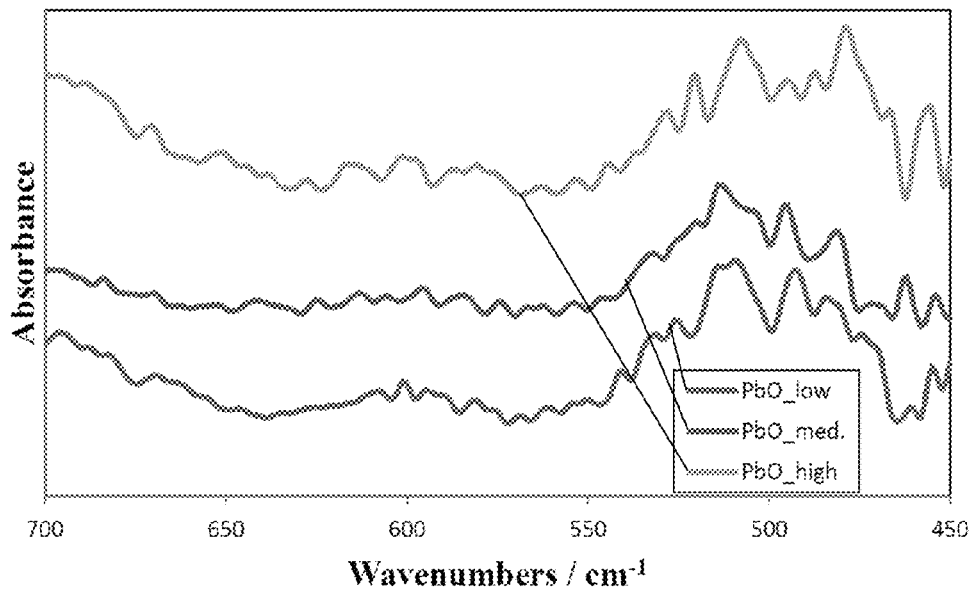
FIG. 13 is a graph that shows FTIR spectra of PbO on the enhanced chicken skin from 450 $cm^{-1}$ to 700 $cm^{-1}$.
Figure 14:
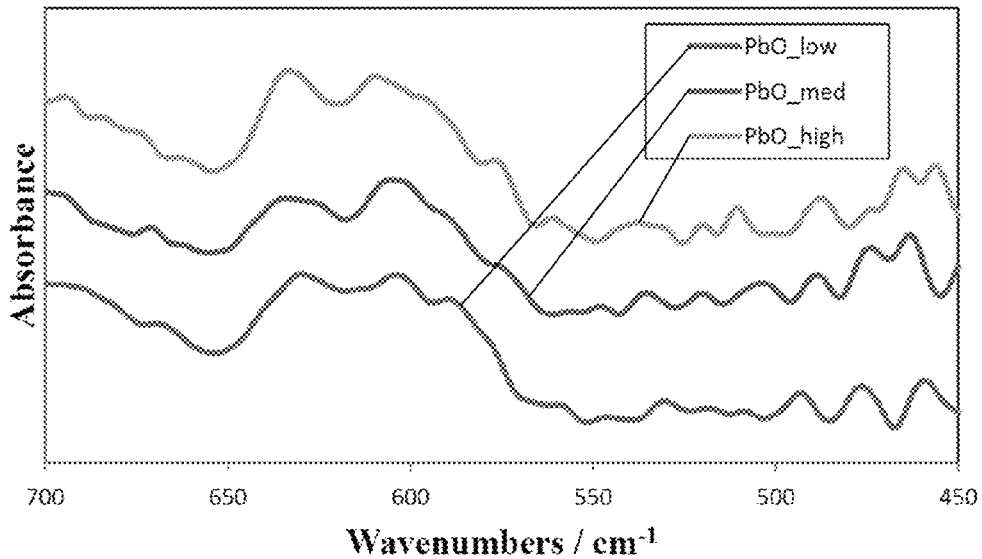
FIG. 14 is a graph that shows FTIR spectra of $PbSO_4$ on the enhanced chicken skin 450 $cm^{-1}$ to 700 $cm^{-1}$.
Figure 15:
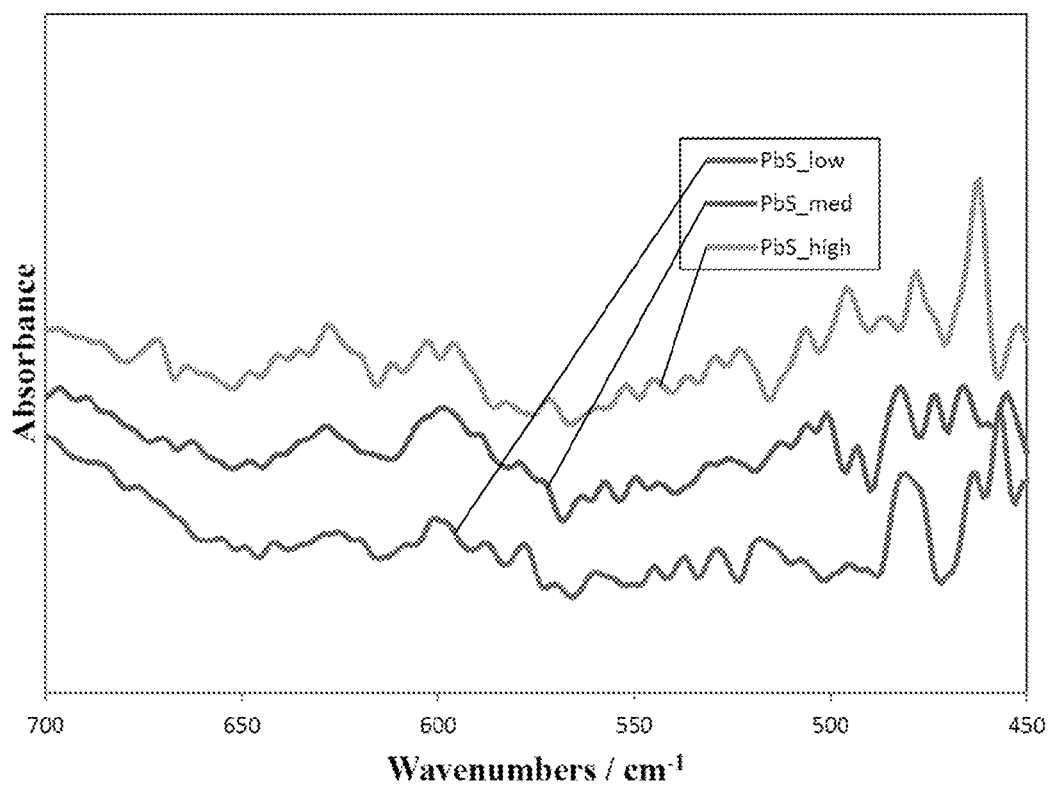
FIG. 15 is a graph that shows FTIR spectra of PbS on the enhanced chicken skin from 450 $cm^{-1}$ to 700 $cm^{-1}$.

The lead contaminants at various concentrations were added to the chicken skin treated with the reflectance medium and FTIR spectroscopy was performed. The results of this spectroscopy are shown in FIGS. 13-15. When these results are compared to the results obtained with the polyethylene membranes, it can be appreciated that the background noise is much higher.

Although olive oil and vegetable oil were used in the above-described experiments, it is noted that other types of oil can be used to create the reflectance medium. For example, the oil can comprise any edible (and therefore harmless) oil, such as olive oil, vegetable oil, canola oil, corn oil, or the like. Furthermore, other liquids, such as polyethylene glycol or any other polyethylene-substituted liquid can be used. It is also noted that metallic particles other than tungsten nanoparticles can be used. For example, the metallic particles can comprise metallic microparticles or nanoparticles that comprise one or more of tungsten, iron, titanium, zinc, aluminum, silver, gold, etc.

As described above, once the spectra are obtained, they can be analyzed to detect and identify the contaminants that are present, if any. During the experimentation, an algorithm was used to detect specific lead ions. The baseline data for the detection of each chemical compound was used to develop a generalized detection algorithm relating the IR signal with appropriate chemical compounds. Using this algorithm, multiple compounds can be efficiently sorted and their respective concentrations can be calculated. This processing can be performed in a matter of a few seconds to a few minutes.

While the above disclosure describes the detection of lead contaminants in detail, it is reiterated that the systems and methods can be used to detect other contaminants. In some embodiments, the systems and methods can be used to detect and quantify any metal contaminant, such as other transition metals (e.g., titanium, iron, cobalt, and manganese), heavy metals (e.g., cadmium, mercury, copper, arsenic, and zinc), and heavy metal oxides, sulfates, halides, and carbonates.

The invention claimed is:

1. A system for detecting the presence of a contaminant on an animal skin surface, the system comprising:
    a liquid reflectance medium configured for application to the skin surface, the reflectance medium being configured to increase an infrared reflectance of the skin surface to facilitate detection of the contaminant;
    an infrared light source configured to shine infrared light on the skin surface;
    an infrared light detector positioned relative to the infrared light source so as to receive infrared light reflected from the skin surface; and
    a computing device configured to receive an infrared reflectance signal from the infrared light detector and detect the presence of the contaminant on the skin surface from a feature in the reflectance signal by identifying one or more peaks in the reflectance signal and correlating the one or more peaks to one or more particular contaminants, the computing device further being configured to determine a concentration of the detected contaminant from the intensity of the reflectance signal.

2. The system of claim 1, wherein the infrared light source emits infrared light in the range of 700 to 200 cm$^{-1}$.

3. The system of claim 1, wherein the infrared light source comprises multiple infrared light emitting diodes each emitting at a different wavelength range within the infrared spectrum.

4. The system of claim 1, wherein the computing device is further configured to identify the detected contaminant to a user.

5. The system of claim 1, wherein the liquid reflectance medium comprises metallic particles suspended in the liquid.

6. The system of claim 5, wherein the metallic particles comprise metallic nanoparticles.

7. The system of claim 1, wherein the contaminant is a metal contaminant.

8. The system of claim 1, wherein the contaminant is a lead contaminant.

9. A method for detecting the presence of a contaminant on an animal skin surface, the method comprising:
    applying a liquid reflectance medium to the skin surface to increase an infrared reflectance of the skin surface and facilitate detection of the contaminant, the reflectance medium comprising a liquid that contains metallic particles;
    illuminating the skin surface with infrared light;
    detecting infrared light reflected from the skin surface; and
    analyzing the reflected infrared light to identify features indicative of the presence of the contaminant on the skin surface, wherein the analyzing comprises identifying a peak in the reflectance signal and correlating the peak to a particular contaminant.

10. The method of claim 9, wherein illuminating the skin surface comprises illuminating the surface with infrared light in the range of 700 to 200 cm$^{-1}$.

11. The method of claim 9, further comprising determining a concentration of the contaminant from the intensity of the reflectance signal.

12. The method of claim 9, wherein the contaminant is a metal contaminant.

13. The method of claim 9, wherein the contaminant is a lead contaminant.

* * * * *